United States Patent
Zhou et al.

(10) Patent No.: US 9,227,889 B2
(45) Date of Patent: Jan. 5, 2016

(54) SWEETENING OF NATURAL GAS

(71) Applicants: Shaojun Zhou, Palatine, IL (US); Howard S. Meyer, Hoffman Estates, IL (US)

(72) Inventors: Shaojun Zhou, Palatine, IL (US); Howard S. Meyer, Hoffman Estates, IL (US)

(73) Assignee: Gas Technology Institute, Des Plaines, IL (US)

( * ) Notice: Subject to any disclaimer, the term of this patent is extended or adjusted under 35 U.S.C. 154(b) by 209 days.

(21) Appl. No.: 13/862,859

(22) Filed: Apr. 15, 2013

(65) Prior Publication Data

US 2014/0309471 A1  Oct. 16, 2014

(51) Int. Cl.
| | |
|---|---|
| *B01D 69/08* | (2006.01) |
| *C07C 7/00* | (2006.01) |
| *B01D 53/14* | (2006.01) |
| *B01D 53/22* | (2006.01) |
| *C10L 3/10* | (2006.01) |

(52) U.S. Cl.
CPC ............ *C07C 7/005* (2013.01); *B01D 53/1443* (2013.01); *B01D 53/1462* (2013.01); *B01D 53/229* (2013.01); *B01D 69/08* (2013.01); *C10L 3/103* (2013.01); *C10L 3/104* (2013.01); *B01D 2053/224* (2013.01); *B01D 2252/20405* (2013.01); *B01D 2256/245* (2013.01); *B01D 2257/304* (2013.01); *B01D 2257/504* (2013.01); *C10L 2290/548* (2013.01); *C10L 2290/567* (2013.01); *Y02C 10/06* (2013.01); *Y02C 10/10* (2013.01)

(58) Field of Classification Search
None
See application file for complete search history.

(56) References Cited

U.S. PATENT DOCUMENTS

| | | | |
|---|---|---|---|
| 2010/0024651 A1* | 2/2010 | Bansal | .............................. 96/13 |
| 2011/0290110 A1 | 12/2011 | Zhou et al. | |
| 2012/0000359 A1 | 1/2012 | Bresler et al. | |
| 2012/0058016 A1 | 3/2012 | Bansal | |
| 2012/0102837 A1* | 5/2012 | Raman et al. | ................ 48/127.7 |
| 2012/0247327 A1 | 10/2012 | Omole | |

FOREIGN PATENT DOCUMENTS

| | | |
|---|---|---|
| GB | 2462178 A | 2/2010 |
| WO | WO 98/04339 | 2/1998 |

OTHER PUBLICATIONS

F. Wiesler, "Membranes, Membrane Contactors: An Introduction to the Technology", Ultrapure Water®, May/Jun. 1996, pp. 27-31, ISSN: 0747-8291, Tall Oaks Publishing, Inc.

* cited by examiner

*Primary Examiner* — Tam M Nguyen
(74) *Attorney, Agent, or Firm* — Pauley Erickson & Kottis

(57) ABSTRACT

An exemplary embodiment can be a process for sweetening natural gas to liquefied natural gas specifications. The process can include providing a membrane contactor having a lumen side and a shell side. A feed natural gas is introduced to the lumen side of the membrane contactor. An absorption solvent is introduced to the shell side of the membrane contactor. $CO_2$ and $H_2S$ are removed with the absorption solvent from the feed natural gas resulting in a sweetened natural gas containing less than 50 ppmv $CO_2$ and less than 4 ppmv $H_2S$. Corresponding or associated systems for such sweetening of natural gas are also provided.

20 Claims, 4 Drawing Sheets

SWEETENING OF NATURAL GAS

BACKGROUND OF THE INVENTION

This invention relates generally to the purification, e.g., sweetening, of natural gas.

Stringent specifications are typically applied to LNG (Liquified Natural Gas) processing. For example, carbon dioxide and often hydrogen sulfide are typically present in field gases and have to be removed to specific levels, e.g., less than 50 ppmv $CO_2$ and less than 4 ppmv $H_2S$) such as due to concerns related to processability, toxicity and corrosion, for example. More particularly, LNG processing typically requires cooling of natural gas to $-160°$ C. This in turn requires that the $CO_2$ concentration in the natural gas be less than 50 ppmv to avoid icing within the system.

Current state of the art processing to achieve such $CO_2$ concentration levels in natural gas is by physical or chemical absorption in a column based process. Alkanolamine absorption process is a current state of art technology for this purpose. These amines are used as aqueous solvents to selectively absorb $H_2S$ and $CO_2$ from sour natural gas streams. The sour gas is introduced at the bottom of an absorber and flows up the tower countercurrent to an aqueous amine stream. Within the tower, the acid gases are absorbed by the amine. The amine is described as being lean in acid gas as it enters the top of the absorber, and rich as it exits the bottom, loaded with acid gas. From the absorber, the rich amine is directed to the top of a stripping tower where a drop in pressure and application of heat enables the solvent to be stripped of the acid gases. The amine, again lean, is circulated back to the absorber for sweetening.

Offshore gas is often dehydrated on the offshore platform. Onshore gas is typically dehydrated a number of times between the well head and the consumer. Triethylene glycol (TEG) dehydrators are commonly the workhorse of the dehydration industry with only sporadic use of molecular sieves or calcium chloride. TEG systems typically circulate water-lean TEG counter-currently to the wet gas to absorb water vapor from the gas. The rich solvent is then heated in a regeneration unit to boil away the water. The lean solvent is returned to the absorber to complete the cycle. The absorber vessels are large towers or columns, 3-5 m in diameter, 10-30 m in height and weighing 50-100 tonnes, depending on throughput. The vessels also have special internals, including trays, random packing, and structured packing, to provide intimate contact between the gas and the liquid.

Conventional absorption towers in both amine sweetening systems and TEG dehydration systems are typically large in size, such as to require a large processing footprint, and heavy in weight. Further, they generally pose operational challenges such as liquid channeling, flooding, entrainment, and foaming.

These and other challenges are often accentuated in a floating LNG application such as may arise in offshore processing such on a ship, barge or platform, and such as may introduce motion parameters to the processing scheme. For example, such applications may suffer from motion-induced inefficiencies and process instability due to maldistribution of solvent in the column.

Thus there is a need and a demand for a processing technique and arrangement that minimizes or overcomes one or more of the process limitations typically associated with the sweetening of natural gas, particularly in the context of offshore applications.

SUMMARY OF THE INVENTION

A general object of one aspect of the invention is to provide an improved process for sweetening natural gas to liquefied natural gas specifications A general object of another aspect of the invention is to provide an improved system for sweetening natural gas to liquefied natural gas specifications, particularly applicable for offshore applications.

A more specific objective of the invention is to overcome one or more of the problems described above.

In accordance with one aspect of the invention, a process for sweetening natural gas to liquefied natural gas specifications involves providing a membrane contactor having a lumen side and a shell side. A feed natural gas is introduced to the lumen side of the membrane contactor. An absorption solvent is introduced to the shell side of the membrane contactor. An absorption solvent is used to remove $CO_2$ and $H_2S$ from the feed natural gas resulting in a sweetened natural gas containing less than 50 ppmv $CO_2$ and less than 4 ppmv $H_2S$.

In accordance with another specific embodiment, there is provided a process for sweetening natural gas to liquefied natural gas specifications on an offshore platform, barge or ship. A hollow fiber membrane contactor having a lumen side and a shell side is provided. A feed natural gas is introduced to the lumen side of the hollow fiber membrane contactor. An absorption solvent is introduced to the shell side of the hollow fiber membrane contactor. $CO_2$ and $H_2S$ are removed from the feed natural gas with the absorption solvent to form a $CO_2$ and $H_2S$ containing solvent stream and a sweetened natural gas stream containing less than 50 ppmv $CO_2$ and less than 4 ppmv $H_2S$. $CO_2$ and $H_2S$ are subsequently stripped from the $CO_2$ and $H_2S$ containing solvent stream to form a regenerated absorption solvent. At least a portion of the regenerated absorption solvent can then be recycled or introduced to the shell side of the hollow fiber membrane contactor.

In another aspect, there is provided an offshore system for sweetening natural gas to liquefied natural gas specifications. In accordance with one embodiment, such a system includes a first membrane contactor having a lumen side for introduction thereinto of a sour natural gas and a shell side for introduction of an absorption solvent. The membrane contactor is effective to remove $CO_2$ and $H_2S$ from the sour natural gas with the absorption solvent to form a $CO_2$ and $H_2S$ containing solvent stream and a sweetened natural gas stream containing less than 50 ppmv $CO_2$ and less than 4 ppmv $H_2S$. The system also desirably includes a second membrane contactor effective to strip $CO_2$ and $H_2S$ from the $CO_2$ and $H_2S$ containing solvent stream to form a regenerated absorption solvent stream.

Moreover, as will be understood and appreciated by those skilled in the art and guided by the teachings herein provided and in accordance with certain specific embodiments, gas sweetening processing conditions such as including one or more of the following process conditions: total inlet gas flow rate, lean solvent $CO_2$ loading, gas inlet pressure, gas inlet temperature, liquid inlet pressure, and liquid inlet temperature, for example, can be appropriately selected such that the practice of the invention herein described permits satisfaction of at least certain LNG specifications, such as relating to $CO_2$ content, for various solvent systems and with various membrane materials and forms.

Other objects and advantages will be apparent to those skilled in the art from the following detailed description taken in conjunction with the appended claims and drawings.

DESCRIPTION OF THE INVENTION

The present invention provides improved processes and systems for sweetening natural gas to liquefied natural gas specifications. As described in greater detail below, such processes and systems can advantageously incorporate and employ a membrane contactor in conjunction with an absorption solvent to remove $CO_2$ and $H_2S$ from a feed natural gas to result in a sweetened natural gas containing desirably reduced amounts of $CO_2$ and/or $H_2S$.

Figure 1:
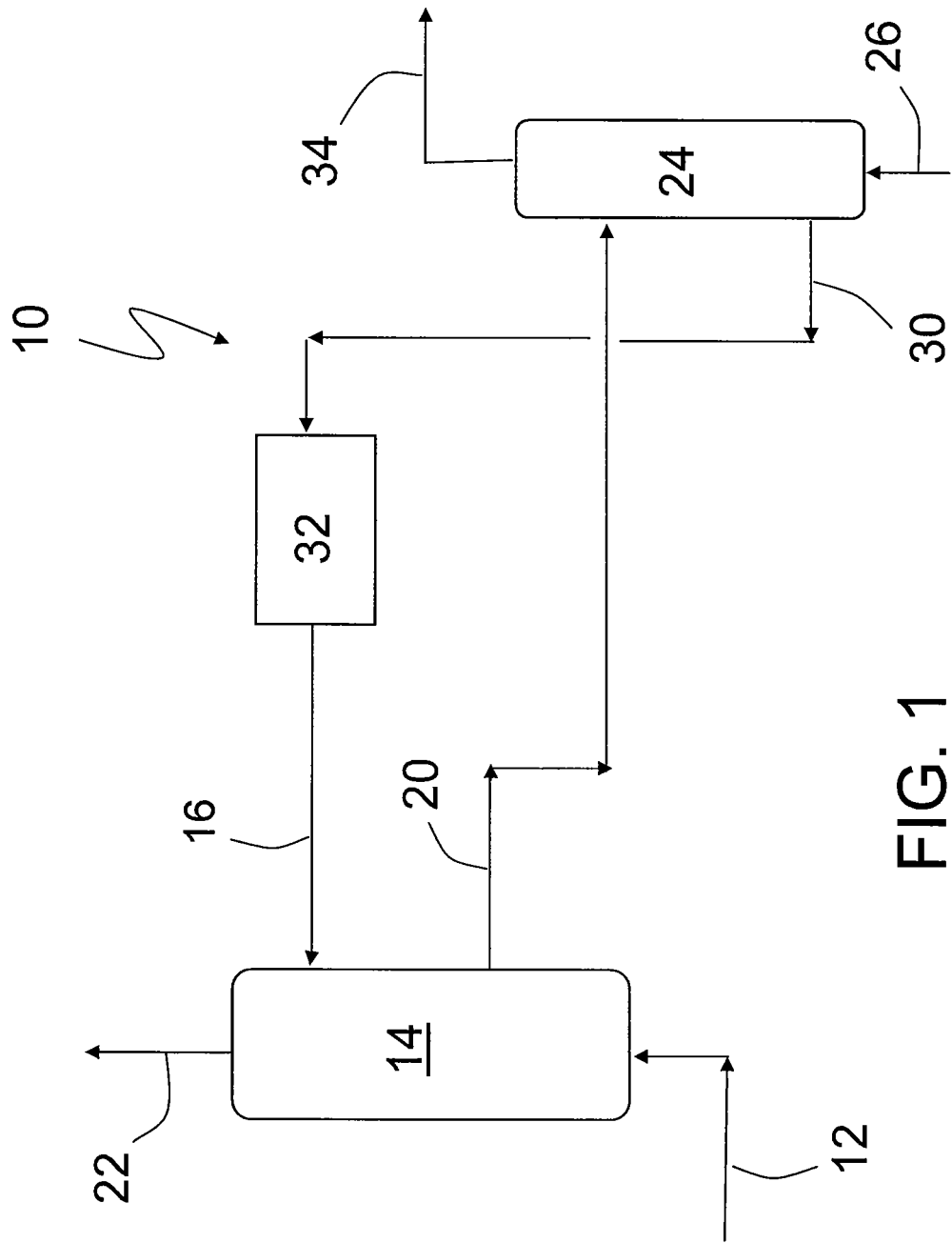
FIG. 1 is a simplified schematic diagram of a system for sweetening natural gas to liquefied natural gas specifications in accordance with one preferred embodiment.

FIG. 1 schematically illustrates a system, generally designated by the reference numeral 10 for sweetening natural gas, for example, desirably to liquefied natural gas specifications, in accordance with one embodiment.

More particularly, a natural gas feedstock or feedstream 12, such as generally composed of a sour natural gas, is introduced into a membrane contactor 14. While the broader practice of the invention is not necessarily limited to use in conjunction with particular or specific natural gas feedstocks or feedstreams, sour offshore natural gas materials typically contain in excess of 3% $CO_2$ and in excess of 50 ppmv $H_2S$, more specifically, such natural gas feed materials generally contain 5% to 40% $CO_2$ and 100 ppmv to 40% $H_2S$.

The membrane contactor 14, such as described in greater detail below and such as generally composed of hollow fibers having a lumen side and a shell side. The feed natural gas is introduced to the lumen side of the membrane contactor 14. The membrane contactor 14 can desirably be operated at ambient conditions of pressure and temperature (e.g., less than 40° C.).

An absorption solvent is introduced to the shell side of the hollow fiber membrane contactor 14 such as via the absorption solvent stream 16. The absorption solvent acts or works upon the feed natural gas to remove $CO_2$ and $H_2S$ from the feed natural gas. More particularly, the absorption solvent acts or serves to remove $CO_2$ and $H_2S$ from the feed natural gas to form a $CO_2$ and $H_2S$ containing solvent stream 20 and such as to result in a sweetened natural gas stream 22 having a desirably reduced content of $CO_2$ and $H_2S$.

As will be appreciated by those skilled in the art and guided by the teachings herein provided, various absorption solvents, such as those known in the art, can be used in the practice of the invention in the removal of $CO_2$ and/or $H_2S$. Examples of suitable solvents that can be used in the practice of the invention include amine solvents. Particularly useful amine solvents for use in the practice of the invention include diethanolamine (DEA) and methyldiethanolamine (MDEA), for example.

The $CO_2$ and $H_2S$ containing solvent stream 20 can, if desired, be appropriately processed so as to regenerate the absorption solvent for recycle and/or reuse. Thus, the system 10 also includes a second membrane contactor, also sometimes referred to as a regenerator or stripper contactor, generally designated by the reference numeral 24 and generally composed of hollow fibers having a lumen side and a shell side wherein the $CO_2$ and $H_2S$ containing solvent stream 20 is introduced to the shell side and a stripping medium, such as steam, for example, is introduced to the bore or lumen side via a stripping medium stream 26. As will be appreciated, with the use of steam as a stripping medium, such a regenerator or stripper contactor will typically operate at a higher temperature than the first membrane contactor wherein $CO_2$ and $H_2S$ are removed from the sour natural gas.

As a result, $CO_2$ and $H_2S$ can be effectively stripped from the $CO_2$ and $H_2S$ containing solvent stream 20 to form a regenerated absorption solvent stream 30, such as can be conveyed to an absorption solvent feed tank or housing 32, and such as for subsequent conveyance to the membrane contactor 14. The steam-stripped $CO_2$ and $H_2S$ form an elevated temperature (e.g., 120° C.) process stream 34 that can be appropriately vented or disposed as may be desired.

Figure 2:
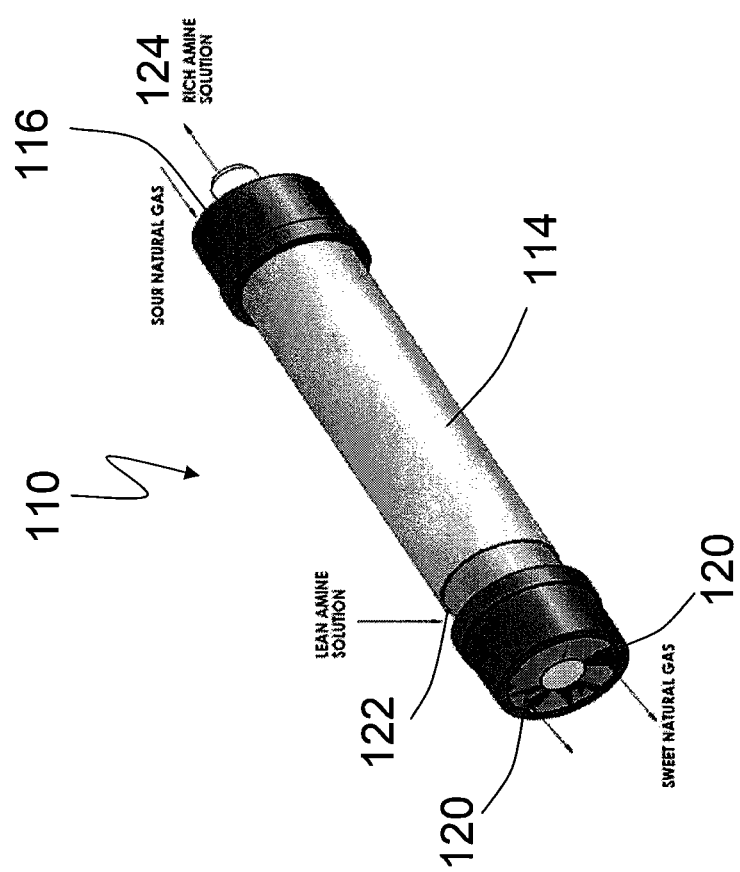
FIG. 2 is a perspective view of a membrane contactor module for sweetening natural gas to liquefied natural gas specifications, in accordance with one aspect of the invention.
Figure 3:
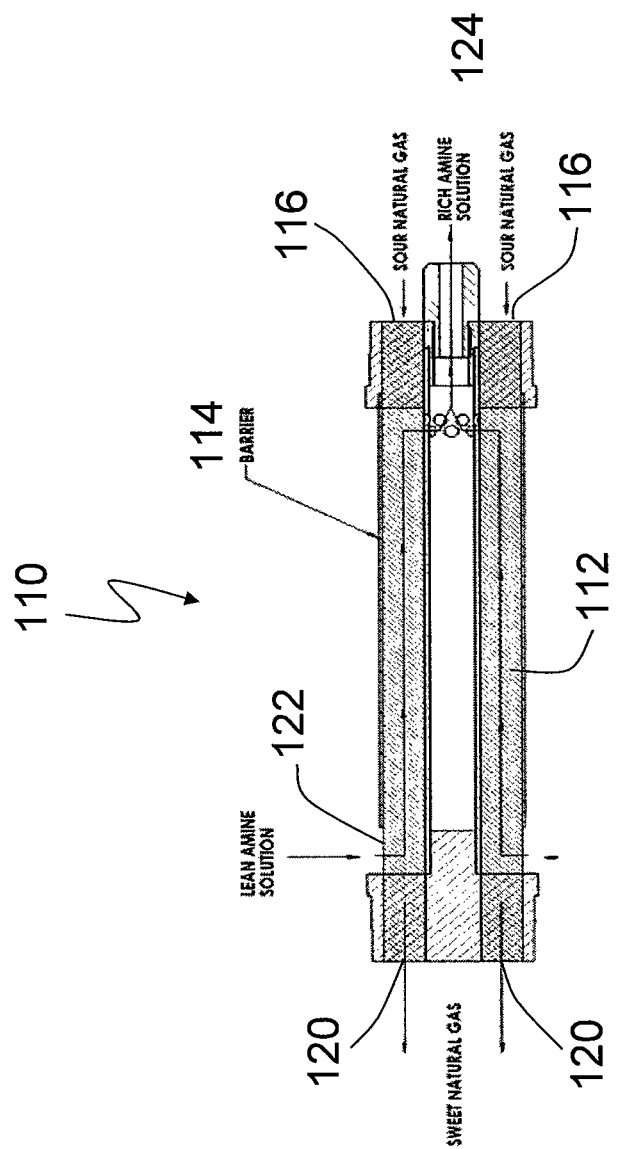
FIG. 3 is a simplified cross sectional schematic of the membrane contactor module shown in FIG. 2.

Turning to FIGS. 2 and 3, there is shown a membrane contactor module, generally designated by the reference numeral 110, and in accordance with one aspect of the invention.

The membrane contactor module 110 is composed of a hollow fiber module of the four-port counter-current flow design. Those skilled in the art and guided by the teachings herein provided will appreciate that while contactor module designs with other flow configurations can, if desired, be used, such counter-current flow configurations can in practice be preferred for improved or increased thermodynamic efficiency.

The membrane contactor module 110 includes a hollow fiber membrane cartridge 112, composed of hollow fiber having a lumen side and a shell side, disposed in a pressure vessel housing 114. The pressure housing 114 includes:

a sour natural gas inlet port 116 wherethrough a sour natural gas-containing stream can be introduced to the lumen side of the hollow fiber membrane;

a sweetened natural gas outlet port 120 wherethrough sweetened natural gas such as containing less than 50 ppmv $CO_2$ and less than 4 ppmv $H_2S$ can be appropriately discharged or released;

a lean absorption solvent inlet port 122 wherethrough one or more selected absorption solvents such as one or more amine solvent such as DEA and/or MDEA can be introduced to the shell side of the hollow fiber membrane; and a rich absorption solvent outlet port 124 wherethrough the selected one or more absorption solvents now rich in $CO_2$ and/or $H_2S$ can be appropriately discharged or released.

Figure 4:
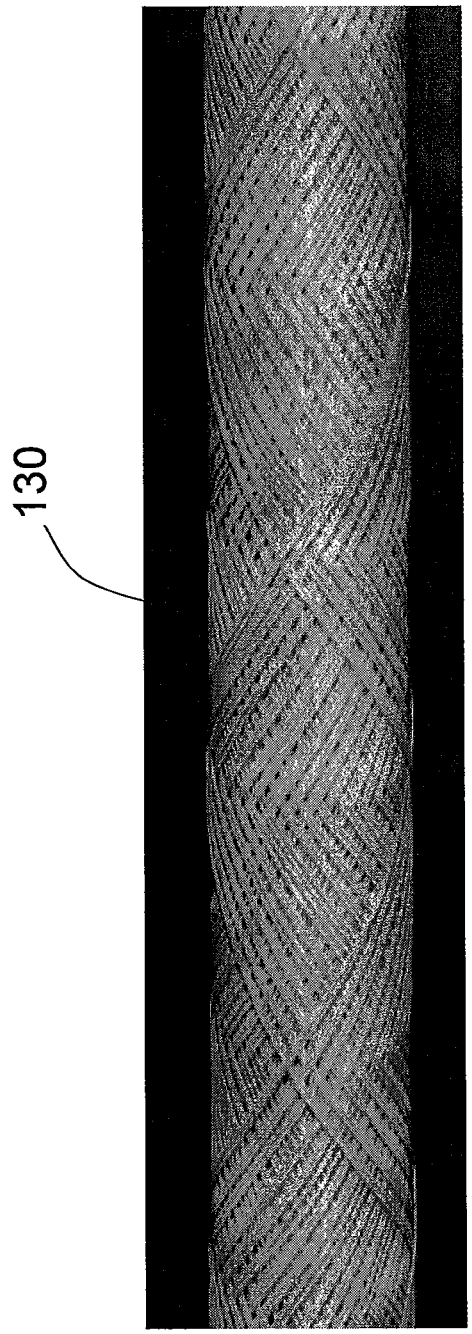
FIG. 4 is a fragmentary view of a helically wound structured hollow fiber cartridge in accordance with one aspect of the invention.

The hollow fiber cartridges for use in the practice of the invention can desirably be formed or fabricated via computer-controlled helical winding. The helical winding process desirably generates a structured packing configuration minimizing channeling, bypassing, and minimizing concentration polarization. A wound cartridge with a controlled uniform structured packing is shown in FIG. 4 and generally designated by the reference numeral 130. The hollow fibers of the cartridge 130 are arranged in a helical path, with the axis of the fibers running confluent to the principle direction of fluid flow. To enable the thermodynamically most efficient counter-current flow, the packing density in the cartridge is preferably uniform. Also, flow bypassing, and entrance and exit effects are desirably minimized. The fiber packing density and packing uniformity can preferably be controlled to ensure an optimal flow distribution with minimal pressure drop on both the feed and the permeate sides.

Various membrane contactors, such as known in the art and including, for example, expanded polytetrafluoroethylene (ePTFE) membrane contactors, can be used in the practice of the invention.

While the broader practice of the invention is not necessarily specifically limited or restricted to use or practice with specific or particular membrane contactors, poly (ether ether ketone) or PEEK-based hollow fiber modules have been found desirable or preferred under certain conditions particularly in view of factors such as relating to processing costs and/or economics.

PEEK materials utilized in such hollow fiber contactors are high-temperature engineered plastics that are extremely resistant to deterioration under the operating conditions encountered in typical gas absorption applications. Further, such PEEK materials desirably can withstand contact with most of the common treating solvents.

Further, in hollow fiber contactors constructed from superhydrophobic PEEK hollow fibers, the hollow-fiber material is extremely hydrophobic with a water breakthrough pressure (differential pressure across the fiber) greater than 600 psig. Such hollow fiber contactors are particularly suited for such applications since the fibers can provide very high surface area to volume ratios and pressures on the bore side and the shell side can be maintained independently, which is customarily not possible for conventional columns.

Further, PEEK hollow fiber absorber modules can be further tailored towards the specific needs of natural gas sweetening to provide improved mass transfer of acid gases from the gas phase to the solvent phase. The robust hollow fibers exhibit a high intrinsic $CO_2$ permeance (>1000 GPU, 1 GPU=$1\times10^6$ ($scm^3$)/($cm^2$ cm Hg sec)) while still providing an absolute gas/liquid inter-phase barrier. As identified above, the contactor module can desirably be constructed using computer-controlled helical winding of the hollow fibers and to provide a compact mass transfer device with high separation efficiency. Further, structured helical packing of the hollow fibers can break the liquid-side boundary layer and reduce concentration polarization. In general, the productivity of such hollow fiber contactors is a function of the mass transfer coefficient, which in turn is controlled by the liquid interface resistance. Therefore, PEEK hollow fiber contactor modules can desirably provide a high mass transfer coefficient by minimizing such liquid interface resistance. For example, PEEK hollow fiber membrane contactors can withstand differential pressures up to 60 psi without significant solvent leakage or structural damage.

As will be appreciated by those skilled in the art and guided by the teachings herein provided, the contacting vessel changes significantly with the use gas/liquid contactor hollow fibers as compared to conventional column-based separation of $CO_2$ or $H_2S$. More specifically, the principle of gas absorption using nanoporous, hollow fiber modules offers several advantages over the use of a conventional packed absorption tower. In a gas absorption contactor system, such as herein provided, the gas flows inside the hollow fibers and the absorption solvent, e.g., amine, flows around the outside of the fibers. The hollow fibers are super-hydrophobic and nanoporous, that is, the solvent will not wet the hollow fiber pores, and the nano-sized pores will remain gas filled. This generally results in extremely low resistance in the open pores to gas flow. Further, the mass transfer generally takes place at pores along the length of the fibers. The separation driving force and component selectivity is set by the solvent/gas chemistry, essentially the same as in the tower.

A significant advantage of using a hollow fiber contactor to separate the phases is that it becomes possible to generally minimize or eliminate the customary or usual limitations of packed towers caused by flooding and entrainment of the liquid by the upward flow of gas. In a hollow fiber contactor in accordance with the invention, the gas and liquid flow can be varied independently, and the contact area will then also be independent of the flow velocities as opposed to the behavior in a tower where the mass transfer area is varying with the liquid load. Thus, hollow fiber modules give the possibility of very high specific contacting areas per unit volume for a hollow fiber contactor (see Table 1, below). Practical considerations, like pressure loss, however, generally limit the value to somewhere between 500 and 3,000 $m^2/m^3$. This is still significantly larger than in a tower where values of 100-250 $m^2/m^3$ are common, and enables significant reductions in contactor volume and weight.

TABLE 1

Gas-liquid contactor device surface area and volumetric mass transfer coefficient comparison

| Gas-liquid contactor | Specific Surface area, ($m^2/m^3$) | Volumetric mass transfer coefficient, (1/sec) |
|---|---|---|
| Packed column (Countercurrent) | 10-350 | 0.0004-0.07 |
| Bubble column (Agitated) | 100-2,000 | 0.003-0.04 |
| Spray column | 10-400 | 0.0007-0.075 |
| Hollow fiber contactor | 100-7,000 | 0.01-4.0 |

Other advantages or benefits associated with or resulting from the use of a hollow fiber contactor can include: reduction, minimization or elimination of foaming and liquid maldistribution (channeling). In addition, the potential of picking-up contaminants can be reduced and thereby decrease the potential or possibility of solvent degradation.

Moreover, tidal- and wave-induced motion, such as may can observed in floating platform and ship applications, desirably does not materially affect the performance of such hollow fiber contactors as compared to performance degradation such as resulting from gas bypass in conventional columns placed in such service or operation.

While deep water natural gas producers may realize the greatest economic benefits from the use of gas/liquid membranes for natural gas sweetening and dehydration in accordance with the invention, processing as herein described also offers potential cost savings via the use of smaller, lower weight, less expensive, easier operated platforms for new gas production in deep Gulf of Mexico waters (greater than 200 feet water depth). Further, additional production from marginal resources may now also be possible because the use of gas/liquid membrane systems as herein described and provided can make production more economical as compared to using conventional absorber technology. Still further, other stranded or remote reserves can also benefit from the smaller processing profile provided herewith such that more practically allows the required mass transfer unit to be contained within a smaller enclosed area. Another benefit is protecting operators from harsh weather conditions. Yet another benefit is a significant reduction in required equipment weight that allows the mass transfer unit to be shop fabricated and requires less installation costs for related foundations and crane deployment.

Thus, the gas/liquid membrane systems herein described offer the natural gas industry an estimated savings of 50-70% reduction in size and weight along with reduced operational difficulties compared to conventional contacting technologies, including trayed and packed columns. They have potential applications in stranded gas resources, both onshore and offshore production operations, as well as in high-pressure gas transmission operations.

Moreover, those skilled in the art and guided by the teachings herein provided will understand and appreciate that membrane absorbers and/or regenerators in accordance with the invention and such as herein described can be oriented horizontally, vertically or otherwise as may be desired in a specific or particular application.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

In these Examples, more than 30 two-inch diameter, 12-inch long cartridge-containing hollow fiber contactor modules with circa 10 ft$^2$ of hollow fiber surface area and having varying physical characteristics of fiber pore size and porosity, fiber dimensions, fiber packing density and fiber surface areas were tested.

Examples 1-6

In these Examples, module performance was tested for $CO_2$ removal utilizing a DEA solvent system. The feed pressure was 500 psig and the feed contained about 8% by volume $CO_2$ with the remainder nitrogen. The $CO_2$ was efficiently removed to generate a product containing less than 2.0 vol. % residual $CO_2$. The gas side pressure drop, the liquid side pressure drop, and the lean and rich loading of the DEA solvent were also measured. The best performing hollow fiber contactor results are summarized in the section below. This module was fabricated with hollow fiber PEEK hollow fibers that had an intrinsic $CO_2$ permeance of 1000 GPU measured using pure $CO_2$ at 30° C.

Test results and mass transfer coefficient calculations for this module are shown in Table 2. The gas-side flow pressure drop, the liquid-side flow pressure, and the lean and rich loading of the DEA solvent for this module are shown in Table 3.

TABLE 2

| Example | Inlet $CO_2$, % | Outlet $CO_2$, % | % Removal | $K_Ga$, mol/(m$^3$ · hr · Kpa) | $K_G$, cm/s | $K_Ga$, 1/s |
|---|---|---|---|---|---|---|
| 1 | 8.03 | 0.08 | 99.1 | 760 | 0.0207 | 0.48 |
| 2 | 7.94 | 1.40 | 83.7 | 1309 | 0.0356 | 0.83 |
| 3 | 7.86 | 1.22 | 85.7 | 1609 | 0.0437 | 1.02 |
| 4 | 7.76 | 2.21 | 73.3 | 1721 | 0.0468 | 1.09 |
| 5 | 8.58 | 2.34 | 74.7 | 1788 | 0.0486 | 1.13 |
| 6 | 7.70 | 1.91 | 76.8 | 1858 | 0.0505 | 1.17 |

TABLE 3

| Example | Lean Loading, mol/mol | Rich Loading, mol/mol | ΔP, gas side, in H$_2$O | ΔP, Liq. side, in H$_2$O |
|---|---|---|---|---|
| 1 | 0.06 | 0.210 | 11.7 | 29.7 |
| 2 | 0.06 | 0.358 | 34.6 | 30.1 |
| 3 | 0.06 | 0.261 | 39.7 | 30.9 |
| 4 | 0.06 | 0.296 | 66.3 | 34.2 |
| 5 | 0.06 | 0.264 | 65.4 | 36.0 |
| 6 | 0.06 | 0.246 | 65.4 | 36.0 |

The overall volumetric mass transfer coefficient measured ranged from 0.48 to 1.17 (1/s). In comparison, an industrial packed column generally has a volumetric mass coefficient range of 0.0004 to 0.07 (1/s). Thus, this subject hollow fiber contactor had a mass transfer coefficient that was 16 times greater than the cited maximum for a packed column. The hollow fiber also had a $CO_2$ gas permeance of about 1000 GPU. Measured mass transfer coefficients in GPU unit are in the range from 500 to 700, suggesting that the mass transfer is not hollow fiber limiting.

Based on the measured mass transfer coefficient, it can be estimated than an 8-inch diameter, full-size commercial module (physical size: 10 inch outer diameter by 60 inch tall) with 1000 ft$^2$ surface area could:

Treat 3.7 MMSCFD from 8.0 vol % inlet to 2 vol % outlet $CO_2$ as projected from performance data with 30 wt % DEA at high pressure using lab scale 2 inch module, and To treat 500 MMSCFD of the same gas, 135 commercial modules are required.

Using a simulation program, it was determined that a trayed column, 1 foot diameter and 40 feet tall, would be required to treat 1 MMSCFD of the gas from 8.0 vol % inlet to 2.0 vol % outlet.

At least an 80% reduction in process equipment volume from a trayed-column to treat an equal amount of gas to the same specification can be realized.

Examples 7-14

In these Examples, module performance was tested for $CO_2$ removal utilizing a DEA solvent system. The gas inlet pressure was 950 psig, the gas inlet temperature was 77° F. and the feed contained about 1% by volume $CO_2$ with the remainder nitrogen. The liquid inlet pressure was 950 psig and the liquid inlet temperature for Examples 7 and 8 was 105° F. and for Examples 9-14 was 78° F.

The hollow fiber contactor results are summarized in Table 4, below.

TABLE 4

| Example | Inlet $CO_2$, vol % | Outlet $CO_2$, ppmv | Total Inlet Gas, SCFH | $K_Ga$, (1/s) | % $CO_2$ Removal |
|---|---|---|---|---|---|
| 7 | 0.963 | 150 ± 10 | 52.6 | 0.016 | 98.5 |
| 8 | 1.104 | 140 ± 10 | 26.4 | 0.008 | 98.7 |
| 9 | 0.963 | 80 ± 9 | 52.5 | 0.016 | 99.0 |
| 10 | 0.984 | 65 ± 6 | 104.9 | 0.032 | 99.3 |
| 11 | 0.983 | 51 ± 5 | 209.9 | 0.065 | 99.4 |
| 12 | 0.960 | 72 ± 10 | 287.9 | 0.089 | 99.2 |
| 13 | 1.270 | 66 ± 7 | 319.0 | 0.099 | 99.5 |
| 14 | 1.150 | 564 ± 20 | 624.6 | 0.176 | 94.3 |

The $CO_2$ was efficiently removed to generate a product containing residual $CO_2$ levels indicating the ability to satisfy LNG specifications, e.g., residual $CO_2$ levels below 100 ppmv, preferably significantly below 100 ppmv, and desirably near or less than 50 ppmv.

Examples 15-22

In these Examples, module performance was tested for $CO_2$ removal utilizing a solvent system composed of 40 wt. % activated MDEA.

The gas inlet pressure was 950 psig, the gas inlet temperature was 70° F. and the feed contained about 1% by volume $CO_2$ with the remainder nitrogen. The liquid inlet pressure was 950 psig and the liquid inlet temperature was 70° F.

The hollow fiber contactor results for these Examples are summarized in Table 5, below.

TABLE 5

| Example | Inlet $CO_2$, vol % | Outlet $CO_2$, ppmv | Total Inlet Gas, SCFH | $K_G a$ (1/s) | % $CO_2$ Removal |
|---|---|---|---|---|---|
| 15 | 0.99 | 160 | 12 | 0.004 | 98.4 |
| 16 | 0.97 | 42 ± 1 | 24 | 0.009 | 99.6 |
| 17 | 0.98 | 50 ± 1 | 48 | 0.018 | 99.5 |
| 18 | 0.98 | 57 ± 2 | 48 | 0.018 | 99.4 |
| 19 | 0.98 | 42 ± 1 | 292 | 0.107 | 99.6 |
| 20 | 1.06 | 569 | 573 | 0.199 | 94.7 |
| 21 | 1.10 | 28 ± 2 | 178 | 0.065 | 99.8 |
| 22 | 0.99 | 340 ± 2 | 413 | 0.147 | 96.6 |

The $CO_2$ was efficiently removed to generate a product containing residual $CO_2$ levels indicating the ability to satisfy LNG specifications, e.g., residual $CO_2$ levels below 100 ppmv, preferably significantly below 100 ppmv, and desirably near or less than 50 ppmv.

Those skilled in the art and guided by the teachings herein provided will understand and appreciate that gas sweetening processing conditions such as one or more of the following process conditions: total inlet gas flow rate, lean solvent $CO_2$ loading, gas inlet pressure, gas inlet temperature, liquid inlet pressure, and liquid inlet temperature, for example, can be appropriately selected to permit attainment of LNG specifications through the practice of the invention herein described.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention. For example and without any unnecessary limitation, the invention can be used for the sweetening of other fuel gases including, for example, biogas, produced via offshore algae farming or otherwise, to LNG specifications.

What is claimed is:

1. A process for sweetening natural gas to liquefied natural gas specifications comprising:
    providing a membrane contactor having a lumen side and a shell side and with a membrane packing configuration to minimize at least one of channeling and bypassing;
    introducing a feed natural gas to the lumen side of the membrane contactor;
    introducing an absorption solvent to the shell side of the membrane contactor; and
    removing $CO_2$ and $H_2S$ with the absorption solvent from the feed natural gas resulting in a sweetened natural gas containing less than 50 ppmv $CO_2$ and less than 4 ppmv $H_2S$.

2. The process of claim 1 wherein the membrane contactor comprises hollow fibers.

3. The process of claim 2 wherein the membrane contactor comprises super-hydrophobic hollow fibers.

4. The process of claim 1 wherein the absorption solvent comprises an amine solvent.

5. The process of claim 4 wherein the absorption solvent comprises DEA.

6. The process of claim 4 wherein the absorption solvent comprises MDEA.

7. The process of claim 1 wherein at least said step of removing $CO_2$ and $H_2S$ with the absorption solvent occurs on a floating platform.

8. The process of claim 7 wherein at least said step of removing $CO_2$ and $H_2S$ with the absorption solvent occurs offshore.

9. The process of claim 1 wherein said removing $CO_2$ and $H_2S$ with the absorption solvent results in a $CO_2$ and $H_2S$ containing solvent stream and said process additionally comprising:
    stripping $CO_2$ and $H_2S$ from the $CO_2$ and $H_2S$ containing solvent stream to form a regenerated absorption solvent; and
    recycling at least a portion of the regenerated absorption solvent to the shell side of the hollow fiber membrane contactor.

10. The process of claim 9 wherein at least said step of stripping $CO_2$ and $H_2S$ from the $CO_2$ and $H_2S$ containing solvent stream occurs on a floating platform.

11. The process of claim 1 wherein the feed natural gas contains in excess of 3% $CO_2$ and in excess of 50 ppmv $H_2S$.

12. The process of claim 11 wherein the feed natural gas contains in 5% to 40% $CO_2$ and 100 ppmv to 40% $H_2S$.

13. A process for sweetening natural gas to liquefied natural gas specifications on an offshore platform, barge or ship, said process comprising:
    providing a hollow fiber membrane contactor having a lumen side and a shell side and with a membrane packing configuration to minimize at least one of channeling and bypassing;
    introducing a feed natural gas to the lumen side of the hollow fiber membrane contactor;
    introducing an absorption solvent to the shell side of the hollow fiber membrane contactor;
    removing $CO_2$ and $H_2S$ from the feed natural gas with the absorption solvent to form a $CO_2$ and $H_2S$ containing solvent stream and a sweetened natural gas stream containing less than 50 ppmv $CO_2$ and less than 4 ppmv $H_2S$;
    stripping $CO_2$ and $H_2S$ from the $CO_2$ and $H_2S$ containing solvent stream to form a regenerated absorption solvent; and
    introducing at least a portion of the regenerated absorption solvent to the shell side of the hollow fiber membrane contactor.

14. The process of claim 13 wherein the feed natural gas contains in excess of 3% $CO_2$ and in excess of 50 ppmv $H_2S$.

15. The process of claim 14 wherein the feed natural gas contains in 5% to 40% $CO_2$ and 100 ppmv to 1000 ppmv $H_2S$.

16. The process of claim 13 wherein the absorption solvent comprises an amine solvent selected from the group consisting of DEA and MDEA.

17. The process of claim 13 wherein the hollow fiber membrane contactor comprises super-hydrophobic hollow fibers.

18. The process of claim 1 wherein said introducing of the feed natural gas to the lumen side of the membrane contactor is countercurrent to said introducing of the absorption solvent to the shell side of the membrane contactor.

19. The process of claim 2 wherein said hollow fibers are arranged in a helical path with an axis of the fibers running confluent to the principle direction of fluid flow.

20. The process of claim 3 wherein said super-hydrophobic hollow fibers comprise PEEK hollow fibers with a water breakthrough pressure greater than 600 psig.

\* \* \* \* \*